US005482708A

United States Patent [19]
Spibey et al.

[11] Patent Number: 5,482,708
[45] Date of Patent: Jan. 9, 1996

[54] FUSION PROTEIN FROM FELINE LEUKAEMIA VIRUS GP70 AS VACCINE

[75] Inventors: Norman Spibey; James O. Jarrett, both of Glasgow, United Kingdom

[73] Assignee: The University Court of the University of Glasgow, Glasgow, United Kingdom

[21] Appl. No.: 175,393

[22] PCT Filed: May 14, 1993

[86] PCT No.: PCT/GB93/00996
§ 371 Date: Feb. 21, 1994
§ 102(e) Date: Feb. 21, 1994

[87] PCT Pub. No.: WO93/23544
PCT Pub. Date: Nov. 25, 1993

[30] Foreign Application Priority Data

May 14, 1992 [GB] United Kingdom ............. 92 10 337.3

[51] Int. Cl.[6] .................. A61K 39/21; A61K 39/385; C07K 14/15; C07K 19/00
[52] U.S. Cl. .................. 424/187.1; 424/192.1; 424/207.1; 530/324; 530/350; 530/806; 530/221
[58] Field of Search ................. 424/89, 187.1, 424/192.1, 207.1; 514/12; 530/324, 350, 806; 930/220, 221

[56] References Cited

U.S. PATENT DOCUMENTS

| | | | |
|---|---|---|---|
| 4,789,702 | 12/1988 | Nunberg | 530/324 |
| 4,794,168 | 12/1988 | Elder et al. | 530/324 |
| 5,152,982 | 10/1992 | Parkes et al. | 424/187.1 |

FOREIGN PATENT DOCUMENTS

| | | |
|---|---|---|
| 0216564 | 4/1987 | European Pat. Off. . |
| 0247904 | 12/1987 | European Pat. Off. . |
| 0293249 | 11/1988 | European Pat. Off. . |
| 0377842 | 7/1990 | European Pat. Off. . |

OTHER PUBLICATIONS

Plotkin, S. A. et al. 1988 *Vaccines*, W. B. Saunders Co., Philadelphia pp. 568–575.
Boswell, P. R. et al. 1988. In: *Computational Molecular Biology*, ed A. M. Lesk, Oxford Univ. Press, pp. 161–178.
Rohn, J. K. et al. 1994, J. Virol. vol. 68 pp. 2458–2467.
J. Brojatsch, et al.; *Feline leukemia virus subgroup C phenotype evolves through distinct alterations near the N terminus of the envelope surface glycoprotein*, Proc. Natl. Acad. Sci. USA, vol. 89, pp. 8457–8461 (Sep. 1992).
J. H. Nunberg, et al.; *Method to map antigenic determinants recognized by monoclonal antibodies: Localization of a determinant of virus neutralization on the feline leukemia virsu envelope protein pg70*, Proc. Natl. Acad. Sci. USA, vol. 81, pp. 3675–3679 (Jun. 1984).

*Primary Examiner*—Mary E. Mosher
*Attorney, Agent, or Firm*—Bell, Seltzer, Park & Gibson

[57] ABSTRACT

A vaccine against feline leukaemia virus (FeLV) comprises a protein formed of two proteins derived from FeLV gp70 which are not adjacent in the native protein, particularly VR1 and VR5 and effective fragments thereof. VR5 is preferably attached to the carboxy terminus of VR1. A co-protein such as GST or β-galactosidase may be attached to the terminus of the fused protein, such as to stabilize and solubilize the fused protein. Attachments to the carboxy terminus may reduce the immunogenicity.

5 Claims, 5 Drawing Sheets

FeLV VR1

```
CCT ACC CTA CAT GTT GAC TTA TGT GAC CTA GTG GGA GAC ACC TGG
Pro Thr Leu His Val Asp Leu Cys Asp Leu Val Gly Asp Thr Trp

GAA CCT ATA GTC CTA AAC CCA ACC AAT GTA AAA CAC GGG GCA CGT
Glu Pro Ile Val Leu Asn Pro Thr Asn Val Lys His Gly Ala Arg

TAC TCC TCC TCA AAG TAT GGA TGT AAA ACT ACA GAT AGA AAA AAA
Tyr Ser Ser Ser Lys Tyr Gly Cys Lys Thr Thr Asp Arg Lys Lys

CAG CAA CAA ACA TAC CCC TTT TAC GTC TGC CCC GGA CAT GCC CCC
Gln Gln Gln Thr Tyr Pro Phe Tyr Val Cys Pro Gly His Ala Pro

TCG CTG GGG CCA AAG GGA ACA CAC TGT G
Ser Leu Gly Pro Lys Gly Thr His Cys
```

FIG. 3

FeLV VR5

| CAG | GCT | TTG | TGC | AAT | AAG | ACA | CAA | CAG | GGA | CAT | ACA | GGG | GCG |
|-----|-----|-----|-----|-----|-----|-----|-----|-----|-----|-----|-----|-----|-----|
| Gln | Ala | Leu | Cys | Asn | Lys | Thr | Gln | Gln | Gly | His | Thr | Gly | Ala |
| CAC | TAT | CTA | GCC | GCC | CCC | AAC | GGC | ACC | TAT | TGG | GCC | TGT | AAC |
| His | Tyr | Leu | Ala | Ala | Pro | Asn | Gly | Thr | Tyr | Trp | Ala | Cys | Asn |
| ACT | GGA | CTC | ACC |
| Thr | Gly | Leu | Thr |

FIG. 4

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
      ( A ) LENGTH: 51 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i x ) FEATURE:
      ( A ) NAME/KEY: CDS
      ( B ) LOCATION: 1..48

( x i ) SEQUENCE DESCRIPTION: SEQ ID NO:1:

| CCA | AAA | TCG | GAT | CTG | GTT | CCG | CGT | GGA | TCC | CCG | GGA | ATT | CAT | CGT | GAC | 48 |
|---|---|---|---|---|---|---|---|---|---|---|---|---|---|---|---|---|
| Pro | Lys | Ser | Asp | Leu | Val | Pro | Arg | Gly | Ser | Pro | Gly | Ile | His | Arg | Asp | |
| 1 | | | | 5 | | | | | 10 | | | | | 15 | | |

TGA                                                                                                                 51

( 2 ) INFORMATION FOR SEQ ID NO:2:

( i ) SEQUENCE CHARACTERISTICS:
      ( A ) LENGTH: 16 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

| Pro | Lys | Ser | Asp | Leu | Val | Pro | Arg | Gly | Ser | Pro | Gly | Ile | His | Arg | Asp |
|---|---|---|---|---|---|---|---|---|---|---|---|---|---|---|---|
| 1 | | | | 5 | | | | | 10 | | | | | 15 | |

( 2 ) INFORMATION FOR SEQ ID NO:3:

( i ) SEQUENCE CHARACTERISTICS:
      ( A ) LENGTH: 208 base pairs
      ( B ) TYPE: nucleic acid
      ( C ) STRANDEDNESS: single
      ( D ) TOPOLOGY: linear ( i i ) MOLECULE TYPE: DNA (genomic)

( i x ) FEATURE:
      ( A ) NAME/KEY: CDS
      ( B ) LOCATION: 1..207

( x i ) SEQUENCE DESCRIPTION: SEQ ID NO:3:

| CCT | ACC | CTA | CAT | GTT | GAC | TTA | TGT | GAC | CTA | GTG | GGA | GAC | ACC | TGG | GAA | 48 |
|---|---|---|---|---|---|---|---|---|---|---|---|---|---|---|---|---|
| Pro | Thr | Leu | His | Val | Asp | Leu | Cys | Asp | Leu | Val | Gly | Asp | Thr | Trp | Glu | |
| 1 | | | | 5 | | | | | 10 | | | | | 15 | | |

| CCT | ATA | GTC | CTA | AAC | CCA | ACC | AAT | GTA | AAA | CAC | GGG | GCA | CGT | TAC | TCC | 96 |
|---|---|---|---|---|---|---|---|---|---|---|---|---|---|---|---|---|
| Pro | Ile | Val | Leu | Asn | Pro | Thr | Asn | Val | Lys | His | Gly | Ala | Arg | Tyr | Ser | |
| | | | 20 | | | | | 25 | | | | | 30 | | | |

| TCC | TCA | AAG | TAT | GGA | TGT | AAA | ACT | ACA | GAT | AGA | AAA | AAA | CAG | CAA | CAA | 144 |
|---|---|---|---|---|---|---|---|---|---|---|---|---|---|---|---|---|
| Ser | Ser | Lys | Tyr | Gly | Cys | Lys | Thr | Thr | Asp | Arg | Lys | Lys | Gln | Gln | Gln | |
| | | 35 | | | | | 40 | | | | | 45 | | | | |

| ACA | TAC | CCC | TTT | TAC | GTC | TGC | CCC | GGA | CAT | GCC | CCC | TCG | CTG | GGG | CCA | 192 |
|---|---|---|---|---|---|---|---|---|---|---|---|---|---|---|---|---|
| Thr | Tyr | Pro | Phe | Tyr | Val | Cys | Pro | Gly | His | Ala | Pro | Ser | Leu | Gly | Pro | |
| | 50 | | | | | 55 | | | | | 60 | | | | | |

```
AAG  GGA  ACA  CAC  TGT  G                                                                              208
Lys  Gly  Thr  His  Cys
 65
```

( 2 ) INFORMATION FOR SEQ ID NO:4:

( i ) SEQUENCE CHARACTERISTICS:
        ( A ) LENGTH: 69 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Pro  Thr  Leu  His  Val  Asp  Leu  Cys  Asp  Leu  Val  Gly  Asp  Thr  Trp  Glu
 1              5                        10                       15

Pro  Ile  Val  Leu  Asn  Pro  Thr  Asn  Val  Lys  His  Gly  Ala  Arg  Tyr  Ser
               20                       25                       30

Ser  Ser  Lys  Tyr  Gly  Cys  Lys  Thr  Thr  Asp  Arg  Lys  Lys  Gln  Gln  Gln
               35                       40                       45

Thr  Tyr  Pro  Phe  Tyr  Val  Cys  Pro  Gly  His  Ala  Pro  Ser  Leu  Gly  Pro
      50                       55                       60

Lys  Gly  Thr  His  Cys
 65
```

( 2 ) INFORMATION FOR SEQ ID NO:5:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..96

( x i ) SEQUENCE DESCRIPTION: SEQ ID NO:5:

```
CAG  GCT  TTG  TGC  AAT  AAG  ACA  CAA  CAG  GGA  CAT  ACA  GGG  GCG  CAC  TAT      48
Gln  Ala  Leu  Cys  Asn  Lys  Thr  Gln  Gln  Gly  His  Thr  Gly  Ala  His  Tyr
 1              5                        10                       15

CTA  GCC  GCC  CCC  AAC  GGC  ACC  TAT  TGG  GCC  TGT  AAC  ACT  GGA  CTC  ACC      96
Leu  Ala  Ala  Pro  Asn  Gly  Thr  Tyr  Trp  Ala  Cys  Asn  Thr  Gly  Leu  Thr
               20                       25                       30
```

( 2 ) INFORMATION FOR SEQ ID NO:6:

( i ) SEQUENCE CHARACTERISTICS:
        ( A ) LENGTH: 32 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Gln  Ala  Leu  Cys  Asn  Lys  Thr  Gln  Gln  Gly  His  Thr  Gly  Ala  His  Tyr
 1              5                        10                       15

Leu  Ala  Ala  Pro  Asn  Gly  Thr  Tyr  Trp  Ala  Cys  Asn  Thr  Gly  Leu  Thr
               20                       25                       30
```

( 2 ) INFORMATION FOR SEQ ID NO:7:

( i ) SEQUENCE CHARACTERISTICS:

(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:7:

GAGGGATCCC TACATGTTGA CTTATG                                26

(2) INFORMATION FOR SEQ ID NO:8:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:8:

TAGGAATTCA CAATGTGTTC CCTTTG                                26

(2) INFORMATION FOR SEQ ID NO:9:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:9:

GACGAATTCC AGGCTTTGTG CAATAAGACA CAA                        33

(2) INFORMATION FOR SEQ ID NO:10:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:10:

TAGGAATTCG CATGCGGTGA GTCCAGTGTT ACA                        33

FUSION PROTEIN FROM FELINE LEUKAEMIA VIRUS GP70 AS VACCINE

FIELD OF THE INVENTION

The present invention relates to an immunogenic fused recombinant protein derived from feline leukaemia virus (FeLV), and to a protective vaccine comprising the immunogenic protein.

BACKGROUND OF THE INVENTION

FeLV is a retrovirus of the sub-family oncovirinae. The virus has a simple genomic organisation with three genes, gag, pol and env, encoding vital proteins.

FeLV occurs in three subgroups, A, B or C, which differ in their env genes. FELV-A is present in every isolate and is efficiently transmitted between cats in nature. Viruses of the other two subgroups arise as variants of FeLV-A in individual cats by recombination of endogenous FeLV env genes (FeLV-B) or mutation within the env gene (FeLV-C). Hence the occurrence of subgroups B or C is dependent upon natural infection of cats with FeLV-A.

FeLV is responsible for several fatal diseases in domestic cats including lymphoid and myeloid leukaemias, fibrosarcomas, anaemia, immunodeficiency, enteritis and reproductive failure. The virus is common in nature: a recent survey in the U.K. indicated that the overall prevalance of infection is approximately 15% of sick cats and 6% in healthy cats. These cats have a persistent infection with viraemia and are a source of infection for susceptible animals. FeLV is transmitted either by contact through the transfer of infectious saliva or prenatally across the placenta.

Following natural or experimental exposure of cats to FeLV, there are two possible outcomes. Cats either develop a persistent, life-long infection or recover. Persistently infected cats have a viraemia while recovered cats have no virus in their blood. Some cats which recover may harbour a latent infection in the bone marrow for several weeks or months before it is eliminated. Recovered cans are immune to FeLV as evidenced by their resistance to subsequent challenge with virus.

Two factors influence the outcome of infection. The first is the age an which a cat is exposed to virus. Kittens up to 14 weeks of age are very susceptible and essentially all can be affected by virus challenge. Older kittens are more resistant so that by 16 weeks of age only about 20% can be infected. The other factor governing susceptibility is dose of virus: high doses lead to persistent viraemia while lower does immunise. The consequences of persistent infection are severe and essentially all viraemic cats die within four years of infection. By contrast recovered cats have a normal life span.

Recovery is due to an immune responsa to the virus. Only antibody responses have been examined in detail. However, it is clear that resistance to reinfection is mediated by virus neutralising antibodies which are directed at the envelope surface glycoprotein the virus, gp70. Attempts have been made to immunise cats against FeLV infection with vaccines containing gp70, some of which have been successful.

European patent specification EP 0377842 describes the production of replication-defective FeLV viral sequences. U.S. Pat. No. 4,794,168 relates to the use of immunogens from FeLV envelope protein P15E in vaccines. European patent specifications 0247904, 0173997 and 0216564, International patent publication WO85/02625 and U.S. Pat. No. 4,789,702 all describe the use of the FeLV envelope protein gp70 or fragments thereof as antigens.

SUMMARY OF THE INVENTION

The present invention is based on the discovery that a fused recombinant protein comprising two regions of the FeLV molecule which are normally non-adjacent, when combined produced an immunogenic determinant capable of inducing anti FeLV antibodies on inoculation into cats. The immunised cats are resistant to challenge with live FeLV.

Thus, the present invention provides an immunogenic fused recombinant protein which comprises:

a first protein which is feline leukaemia virus (FeLV) gp70 VR1 protein (SEQ ID NO:4) or effective fragment thereof, having fused thereto;

a second non-adjacent FeLV protein or effective fragment thereof different from the first protein and capable of stabilising the first protein, such that said fused recombinant protein is immunogenic and protective against FeLV infection.

It has been found that the use of gp70 VR1 protein alone, whilst producing antibodies, is not protective against FeLV infection.

It has however been found that the fusion of a second non-adjacent FeLV protein (or fragment thereof) may result in a fused recombinant protein which is both antigenic and protective against FeLV infection. The second protein is preferably also derived from gp70. In particular, the gp70 VR5 protein (SEQ ID NO:6) (or fragment thereof), which may not by itself produce antibodies, is capable of stabilising the first protein and producing a fused protein which surprisingly has immunogenic and protective properties.

Preferably, the second protein is fused to the carboxy terminus of VR1.

Usually, the fused recombinant protein will be free of glycosylation.

The fused recombinant protein, preferably further comprises an antigenic co-protein, such as Glutathione-S-transferase (GST) or beta-galactosidase. relatively large co-proteins solubilise the protein and facilitate production and purification thereof. Moreover, the co-protein may act as an adjuvant in the sense of providing a generalised stimulation of the immune system. Preferably the co-protein is attached to the amino terminus of the fused protein.

Surprisingly, it has been found that co-proteins (such as GST or β-galactosidase) may be attached to the amino terminus of the fused protein without adversely affecting immunogenicity thereof, and imparting desirable solubility and stability properties. However, it has been found that the attachment of other proteins to the carboxy terminus (whilst being useful in stabilising the fusion protein against egradation during preparation) may adversely affect its immunogenicity. It is postulated that this may be due to conformational changes brought about by the presence of the co-protein attached at the carboxy terminus. Therefore any co-protein attached at the carboxy terminus should be relatively small such as not to disturb the antigenic conformation of the fusion protein.

The present invention also provides a vaccine formulation which comprises the immunogenic fused recombinant protein together with a suitable carrier. Since the protein may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient: and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use.

The vaccine formulation may also include adjuvant systems for enhancing the immunogenicity of the formulation, such as oil-in water systems and other systems known in the art.

The dosage will depend on the specific activity of the vaccine and can be readily determined by routine experimentation.

The present invention also provides a method of constructing a fused recombinant protein which comprises:

introducing a DNA sequence coding for the first protein (SEQ ID NO:3) into a plasmid;

opening the plasmid and introducing a DNA sequence coding for the second protein (SEQ ID NO:5) adjacent the first DNA sequence, and expressing the recombinant protein.

In particular, the DNA sequences may be amplified using polymerase chain reaction (PCR). The amplified sequences may then be inserted one after another into adjacent positions in the plasmid. The plasmid may also include a gone coding for GST or similar co-protein.

The plasmid thus constructed may be expressed in any suitable bacteria, such as E. coil.

Whilst the invention has been described with reference to certain named proteins, such as gp70 VR1 and VR5 proteins, it is to be understood that this covers fragments of the naturally occurring protein and similar proteins (for example, having sequence homologies of 50% or greater) with additions, deletions or substitutions which do not substantially affect the immunogenic properties of the fused recombinant protein.

The second protein is one which does not normally lie adjacent to the first protein in the native FeLV gp70 protein. Non-adjacent means that it is not adjacent in the linearised amino acid sequence.

DESCRIPTION OF PREFERRED EMBODIMENTS

Embodiments of the present invention will now be described by way of example only with reference to following figures and examples.

BRIEF DESCRIPTION OF THE DRAWINGS

FIG. 3 shows the native FeLV gp70 VR1 sequence (SEQ ID NO:3);

FIG. 4 shows the native FeLV gp70 VR5 sequence (SEQ ID NO:5); and

Figure 1:
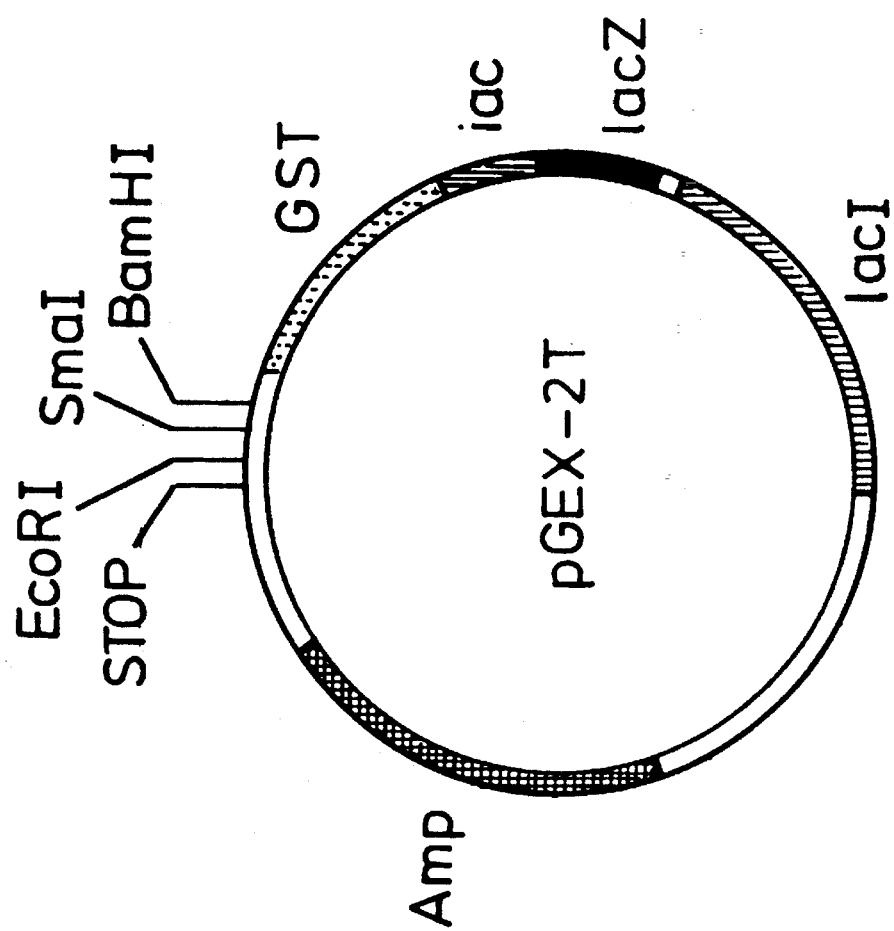
FIG. 1 shows the plasmid pGEX-2T employed in the construction of the fused recombinant protein.
Figure 2:
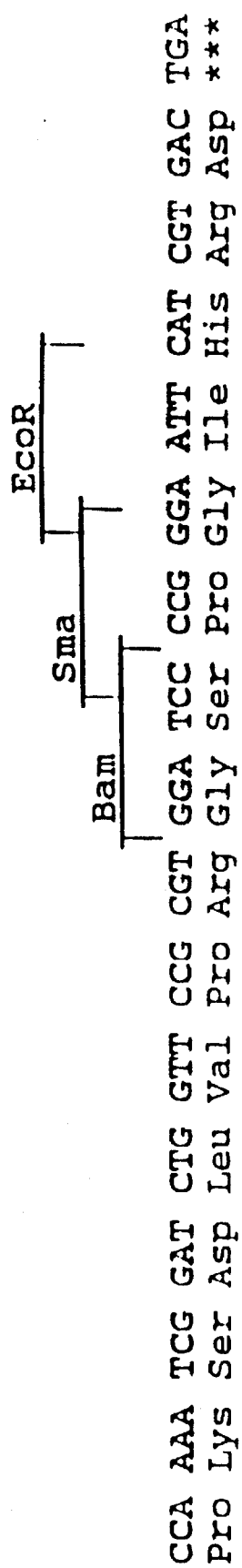
FIG. 2 shows a terminal sequence including restriction sites (SEQ ID NO:1)
Figure 5:
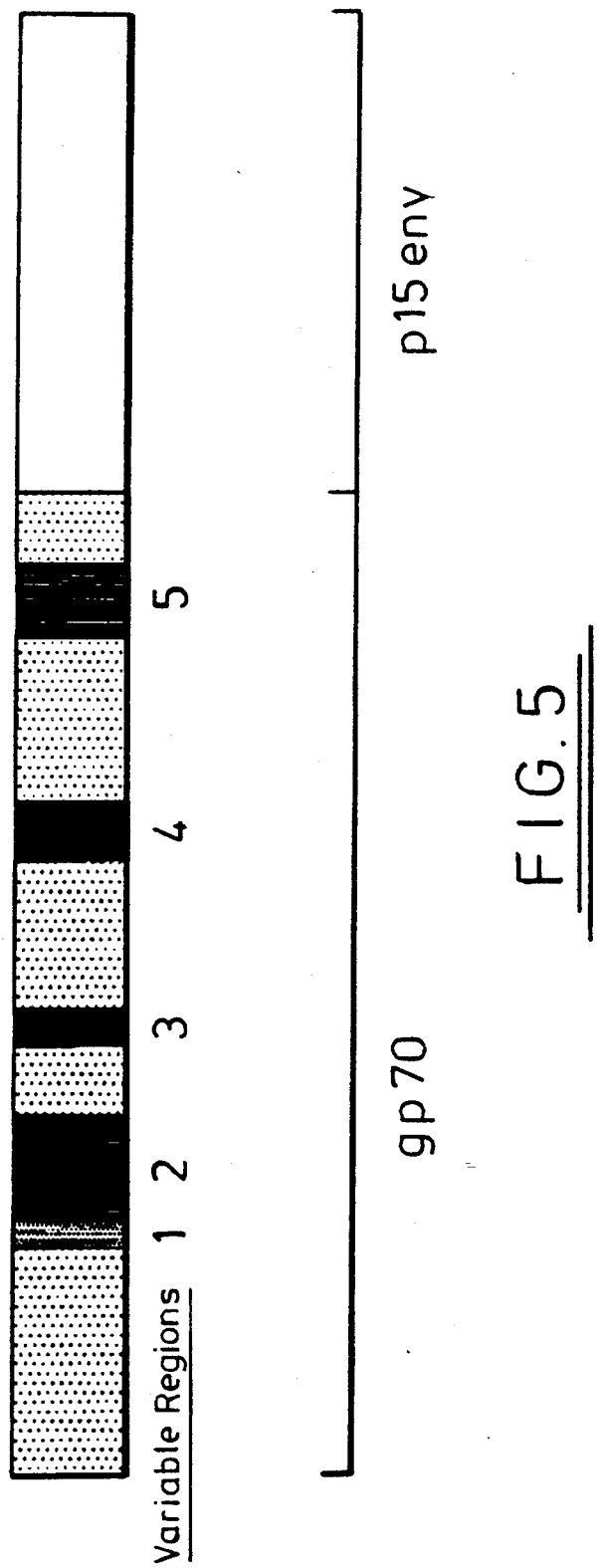
FIG. 5 is a diagrammatic representation of the variable regions in the FeLV gp70 gene.

The following examples illustrate the construction and immunogenic properties of the fused recombinant protein GST-VR1-VR5.

EXAMPLE 1

Construction of a Plasmid Expressing Recombinant gp70 Fusion Protein

The cloning vector used for these experiments is pGEX-2T (Smith & Johnston, Gene 67 (1988) 31–40). The FeLV gp70 gone fragment is cloned into this plasmid to produce a polypeptide fused to the —COOH terminus of the enzyme Glutathione-S-transferase (GST). Previous experiments have demonstrated that large fragments of gp70 (over 20kd) often result in problems of insolubility and degradation. In an attempt to circumvent these problems it was decided to express a range of smaller gp70 fragments. Furthermore, the regions chosen for expression are some of the "variable" regions of gp70, i.e. those regions showing the greatest variation between sub-groups A, B and C.

The region of the FeLV gp70 gone containing VR1 was amplified using the following primers. The cloned envelope gene was the template used.

1) 5' GAG GGA TCC CTA CAT GTT GAC TTA TG 3' (SEQ ID NO: 7)
   BamHI 2) 5' TAG GAA TTC ACA ATG TGT TCC CTT TG 3' (SEQ ID NO: 8)
   EcoRI

The PCR product was digested with the restriction enzymes BamHI and EcoRI the sites for which had been incorporated into the primers as shown above. There are no sites for these two restriction enzymes within the amplified fragment.

The digested PCR product was separated, by electrophoresis on an agarose gel, from any contaminating by products of the PCR reaction. The section of the agarose gel containing the DNA fragment was excised and the DNA removed by electroelution. After ethanol precipitation the DNA fragment was cloned into BamHI/EcoRI cut pGEX-2T.

After transformation of a recipient E.coli strain, clones harboring a recombinant pGEX-2T/VR1 plasmid were isolated.

The following primers were used to amplify a DNA fragment spanning the VR5 region:

5' GAC <u>GAA TTC</u> CAG GCT TTG TGC AAT AAG ACA CAA 3' (SEQ ID NO: 9)
     EcoRI

5' TAG <u>GAA TTC GCA TGC</u> GGT GAG TCC AGT GTT ACA 3' (SEQ ID NO: 10)
     EcoRI SphI

Cloned FeLV gp70 gene was again the template used, the PCR product was digested with EcoRI prior to purification on agarose. This PCR product was cloned into the pGEX-2T/VR1 plasmid described above. Clones carrying VR5 in the correct orientation with respect to VR1 were identified both by DNA sequence analysis and restriction enzyme analysis.

EXAMPLE 2

Preparation of GST-VR1VR5 Recombinant Protein

The glutathione-S-transferase (GST) of Schistosoma japonicum is a small, very soluble enzyme which is tolerant of insertions at its carboxyl end. The gene (Sj26) encoding for this enzyme has been placed under the control of an inducible promoter and introduced into a plasmid together with an ampicillin resistance marker on it. A multiple restriction site has been introduced at the 3' end of Sj26, in tandem with a region coding for a thrombin cleavage site. The resulting plasmid (pGEX-2T) can produce large quantities of a fusion protein, which is extractable using affinity chromatography. The fusion protein is cleavable and the resulting peptide can be purified by repeating the affinity chromatography.

The following materials and methods are part of routine laboratory practice and can be found in "Molecular Cloning, A Laboratory Manual" second edition, Eds. Sambrook, Fritsch and Maniatis. and also in "Current Protocols in Molecular Biology." Below is a detailed description of the materials and methods used.

Materials
Enriched L Broth
100 ml L Broth
1 ml 2M glucose
1 ml 1M mgCl$_2$
200x IPTG
1 g isopropyl D thio-galactopyranoside (IPTG)
8 ml water make up to 10 ml
Filter sterilise, dispense into aliquots of 0.5 ml, freeze at −20° C.
1000x PMSF in isopropanol
1 mg/ml phenyl methyl sulphonyl fluoride
20% TX100
2 ml TX100
8 ml water
Filter sterilise. Easier to handle at this concentration.
Glutathione/Tris
250 ml 1.0M Tris
4.75 ml water
30.73 mg glutathione
Filter sterilise.

a) Preparation of glutathione beads

A 15 ml polypropylene tube is taken and 70 mg of dehydrated glutathione agarose beads are swollen with 10 mls of PBS/1% TX100 using gentle agitation for 30 minutes.

They are then precipitated at 2000 rpm for 5 minutes. The beads are resuspended in 5 mls of PBS to wash them, this procedure is repeated three times. (PBS/1%TX100 or PBS/tween are valid alternatives).

b) Production of Fusion Protein

1. Bacterial cells, transfected with a recombinant pGEX plasmid containing the DNA coding for the protein of interest, are cultured in 100 mls of enriched L Broth overnight in the presence of ampicillin.

2. The overnight culture is inoculated into 900 mls of enriched L Broth (with ampicillin). The bacterial suspension is grown up with vigorous shaking to an O.D of approximately 0.6 (550 nm) (about 2 hours) then IPTG is added to a final concentration of 50ug/ml. The culture is left for a further 90 minutes. Whilst inducing the culture, stare to prepare the swollen, washed glutathione beads for use in stage 5 below.

3. The culture is then centrifuged at 6000 rpm for 15 minutes. The supernatant is discarded. The pellets are resuspended in 10 mls of PBS/1% TX100. 10 ul of PMSF in isopropanol is added.

4. The concentrated bacterial suspension is sonicated in ice for 30 seconds and then centrifuged at 18000 rpm for 15 minutes. The supernatant is retained.

5. The beads are then resuspended in the supernatant from step 4 above and 20% TX100 added to a final concentration of 1% TX100. The mixture is gently agitated for 1 hour.

6. The mixture is centrifuged at 2000 rpm for 15 minutes and the beads washed 3 tiles as before. One ml of the solution of 20 mM glutathione/50 mM Tris is added to the beads and left for 30 minutes. The beads are again centrifuged out (the supernatant being retained) and washed once using another 1 ml of the above glutathione solution. The washing is added to the supernatant.

7. The supernatant contains the fusion protein. An aliquot should be retained to verify this. The supernatant is then dialysed overnight in PBS to remove the excess glutathione. It may then be frozen at −200° C.

The preparation exhibited a degree of degradation and/or incomplete synthesis. Nevertheless sufficient material from a 2 liter culture was obtained to conduct these experiments (4 mg. total protein).

EXAMPLE 3

Vaccination

Since young kittens are most at risk of FeLV infection, the immunisation regime is designed to test the capacity of a vaccine to protect kittens at an early age, and to be compatible with the timing of vaccination against other feline viruses.

The route of challenge is by the oronasal route to simulate natural horizontal transmission of FeLV. A dose of virus is used which will cause persistent viraemia in over 90% of 14 week old kittens.

The schedule of vaccination and monitoring is in Table 1 . The response of the kittens to vaccination challenge is given in Table 2.

The VR1-VR5 preparation elicited an immune response. A large proportion of the antibodies raised are directed against the GST portion of the recombinant as measured by ELISA. However, a competition ELISA using native GST and the recombinant protein also indicates that the immunised cats also responded to the FeLV component of the recombinant protein.

Western blot analysis using FeLV as antigen shows that three out of the four VR1-VR5 treated cats (59,61,62) produced easily detectable anti-gp70 antibodies and cat 60 gave a weak response on Western analysis. All controls were negative.

Virus neutralising antibodies were found in one cat prior to challenge and in a further 2 of the 4, four cats 6 weeks post challenge.

Three of the four vaccinated cats (59,61,62) were also found to be negative for virus isolation 3, 6 and 9 weeks post challenge, whilst all 4 control animals developed viraemia.

The cats responses to immunisation and challenge show that the VR1-VR5 preparation is able to produce an anti-gp70 antibody response and protect the animals from virus challenge.

TABLE 1

SCHEDULE OF VACCINATION AND SAMPLING

| Age of Kitten (weeks) | Week from challenge | Event |
|---|---|---|
| 9 | −5 | Blood sample Vaccination-1 |
| 12 | −2 | Blood sample Vaccination-2 |
| 14 | 0 | Blood sample Challenge |
| 17 | 3 | Blood sample |
| 20 | 6 | Blood sample |
| 23 | 9 | Blood sample |

TABLE 2

(VACCINATION RESULTS)

| | | TIME (WEEKS) RELATIVE TO CHALLENGE | | | | | | | | | | | | | | |
|---|---|---|---|---|---|---|---|---|---|---|---|---|---|---|---|---|
| | CAT | −5 | | | | | −2 | | | | | 0 | | | | |
| GROUP | F | *A | V | N | E | W | A | V | N | E | W | A | V | N | E | W |
| VR-1 + 5 | 59 | − | − | 0 | | | − | − | 0 | | | − | − | 0 | + | + |
| | 60 | − | − | 0 | | | − | − | 0 | | | − | − | 0 | − | W |
| | 61 | − | − | 0 | | | − | − | 0 | | | − | − | 0 | + | + |
| | 62 | − | − | 0 | | | − | − | 0 | | | − | − | 4 | + | + |
| CONT | 67 | − | − | 0 | | | − | − | 0 | | | − | − | 0 | − | − |
| | 68 | − | − | 0 | | | − | − | 0 | | | − | − | 0 | − | − |
| | 69 | − | − | 0 | | | − | − | 0 | | | − | − | 0 | − | − |
| | 70 | − | − | 0 | | | − | − | 0 | | | − | − | 0 | − | − |

| | | TIME (WEEKS) RELATIVE TO CHALLENGE | | | | | | | | | | | | | |
|---|---|---|---|---|---|---|---|---|---|---|---|---|---|---|---|
| | CAT | 3 | | | | | 6 | | | | | 9 | | | |
| GROUP | F | A | V | N | E | W | A | V | N | E | W | A | V | N | E |
| VR-1 + 5 | 59 | − | − | | | | − | − | | | | + | − | − | 0 | |
| | 60 | + | + | | | | + | + | | | | − | + | + | 0 | |
| | 61 | − | − | | | | − | − | | | | + | − | − | 128 | |
| | 62 | − | − | | | | − | − | | | | + | − | − | 128 | |
| CONT | 67 | + | + | | | | + | + | | | | + | + | + | 0 | |
| | 68 | + | + | | | | + | + | | | | − | + | + | 0 | |
| | 69 | + | + | | | | + | + | | | | + | + | + | 0 | |
| | 70 | + | + | | | | + | + | | | | − | + | + | 0 | |

*A = p27 antigen in plasma
V = Virus isolated from plasma
N = Virus neutralising antibody
E = anti-gp70 antibody (ELISA)
W = anti-gp70 antibody (Western blot)

We claim:

1. An immunogenic fused recombinant protein which comprises a feline leukemia virus (FeLV) gp70 VR5 sequence fused to the carboxy terminus of a FeLV gp70 VR1 sequence, wherein the VR5 sequence has the sequence of SEQ ID NO: 6, and the VR1 sequence has the sequence of SEQ ID NO: 4.

2. A fused recombinant protein according to claim 1 which further comprises the sequence of an antigenic co-protein, said antigenic co-protein sequence attached to the amino terminus of said fused protein sequence.

3. A fused protein according to claim 2 wherein the co-protein sequence is glutathione-S-transferase of β-galactosidase.

4. A vaccine formulation which comprises the fusion protein of claim 1 together with a pharmaceutically acceptable carrier.

5. A vaccine formulation which comprises the fusion protein of claim 2 together with a pharmaceutically acceptable carrier.

* * * * *

UNITED STATES PATENT AND TRADEMARK OFFICE
CERTIFICATE OF CORRECTION

PATENT NO. : 5,482,708
DATED : January 9, 1996
INVENTOR(S) : Norman Spibey and James O. Jarrett It is certified that error appears in the above-identified patent and that said Letters Patent is hereby corrected as shown below:

Column 1, Line 41, delete "cans" and insert --cats--.

Column 1, Line 45, delete "an" and insert --at--.

Column 1, Line 55, delete "responsa" and insert --response--.

Column 2, Line 42, delete "relatively" and insert --These relatively--.

Column 3, Line 39, delete "gone" and insert --gene--.

Column 5, Line 44, delete "200x" and insert --2000x--.

Column 6, Line 20, delete "stare" and insert --start--.

Column 6, Line 34, delete " tiles" and insert --times--.

Column 6, Line 66, after "recombinant" insert --molecule--.

Signed and Sealed this

Ninth Day of July, 1996

BRUCE LEHMAN

*Attest:*

*Attesting Officer*    *Commissioner of Patents and Trademarks*